United States Patent [19]

Edwards et al.

[11] Patent Number: 6,133,467
[45] Date of Patent: Oct. 17, 2000

[54] 2,6-DI-T-BUTYL-4-[(DIMETHYL-4-METHOXYPHENYLSILYL)-METHYL-OXY] PHENOL AND 2,6-DI-T-BUTYL-4-[(DIMETHYL-2-METHOXY-PHENYLSILYL) METHYLOXY]PHENOL

[75] Inventors: Michael L. Edwards, Morristown, N.J.; Mark J. Vaal, Baltimore, Md.; Roger A. Parker, Cincinnati, Ohio; James E. Matt, Indianapolis, Ind.; Kim S. Chen, San Diego, Calif.; Mark T. Yates, Ann Arbor, Mich.

[73] Assignee: Hoechst Marion Roussel, Inc., Somerville, N.J.

[21] Appl. No.: 09/103,215

[22] Filed: Jun. 23, 1998

Related U.S. Application Data

[60] Provisional application No. 60/080,226, Jun. 25, 1997.

[51] Int. Cl.[7] .................................................. C07F 7/04
[52] U.S. Cl. .................................................. 556/445
[58] Field of Search ............................................ 556/445

[56] References Cited

U.S. PATENT DOCUMENTS

| | | |
|---|---|---|
| 3,129,262 | 4/1964 | Laufer . |
| 3,576,883 | 4/1971 | Neuworth . |
| 3,786,100 | 1/1974 | Neuworth . |
| 3,862,332 | 1/1975 | Barnhart . |
| 3,897,500 | 7/1975 | Neuworth . |
| 4,000,265 | 12/1976 | Quillichini . |
| 4,663,314 | 5/1987 | Hayse . |
| 4,670,421 | 6/1987 | DeVries . |
| 4,719,237 | 1/1988 | McCaughan . |
| 4,734,527 | 3/1988 | Krauss . |
| 4,772,363 | 9/1988 | Van Effen . |
| 4,861,443 | 8/1989 | Van Effen . |
| 4,870,101 | 9/1989 | Ku . |
| 4,900,757 | 2/1990 | Mao . |
| 4,975,467 | 12/1990 | Ku . |
| 5,008,421 | 4/1991 | Brownell . |
| 5,061,734 | 10/1991 | Mao . |
| 5,112,870 | 5/1992 | Mao . |
| 5,155,250 | 10/1992 | Parkert . |
| 5,217,870 | 6/1993 | Hession . |
| 5,272,263 | 12/1993 | Hession . |
| 5,281,738 | 1/1994 | Parker . |
| 5,304,668 | 4/1994 | Parker . |
| 5,356,917 | 10/1994 | Panetta . |
| 5,367,056 | 11/1994 | Hession . |
| 5,380,747 | 1/1995 | Meford . |
| 5,401,883 | 3/1995 | Laskovics . |
| 5,532,400 | 7/1996 | Parker . |
| 5,608,095 | 3/1997 | Parker . |
| 5,677,291 | 10/1997 | Mao et al. . |

FOREIGN PATENT DOCUMENTS

| | | |
|---|---|---|
| 9460533 | 4/1993 | Australia . |
| 0374048 | 12/1989 | European Pat. Off. . |
| 0372542 | 6/1990 | European Pat. Off. . |
| 0464844 | 1/1992 | European Pat. Off. . |
| 0464852 | 1/1992 | European Pat. Off. . |
| 7330595 | 12/1995 | Japan . |
| 1199871 | 5/1978 | United Kingdom . |
| 9312089 | 6/1993 | WIPO . |
| 9321914 | 11/1993 | WIPO . |
| 9405333 | 3/1994 | WIPO . |
| 9409772 | 5/1994 | WIPO . |
| 9411027 | 5/1994 | WIPO . |
| 9414786 | 7/1994 | WIPO . |
| 9416094 | 7/1994 | WIPO . |
| 9417828 | 8/1994 | WIPO . |
| 9504749 | 2/1995 | WIPO . |
| 9515760 | 6/1995 | WIPO . |
| 9740837 | 11/1997 | WIPO . |

OTHER PUBLICATIONS

Bioorganic & Medicinal Chemistry Letters, Boger, Ed., vol. 6, No. 13, Jul. 9, 1996, pp. 1559–1562.
Gotteland et al, J. Med. Chem., 1995, 38, pp. 3207–3216.
Pilewski et al, Am. J. Respir. Cell Mol. Biol. vol. 12, pp. 1–3, 1995.
Marui et al, American Society for Clinical Investigation, Inc. vol. 92, Oct., 1993, pp. 1866–1874. Vascular Cell adhesion Molecule–1.
Boschelli et al, J. Med. Chem. 1995, 38, pp. 4597–4614. Inhibition of E–Selection–,ICAM–1–, and VCAM–1–.
Derwent Abstract, 94–322148/40.
Derwent Abstract, 94–322152/40.
Abstract 009, Pres. made at 211th ACS National Meeting, Mar. 24–28, 1996, Medicinal Chemical Division. Ref. Bioorganic & Medicincal Chemistry Letter, vol. 6, pp. 533–538, 1996.
Derwent Abstract, 94–325887/41, 1994.
Alerting Bulletin 92–324750/49 Abbreviated Abstract for JP06505732–W, 1992.
Alerting Bulletin 92–332847/41 Abbreviated Abstract for JP06505735–W, 1992.
Parthasarathy, et al, "Probucol inhibits oxidative modification of low density lipoprotein", J. Clin. Invest., vol. 77, Feb. 1986, pp. 641–644.
Product Labeling for Lorelco, Physician's Desk Reference, 42nd edition, (1988), Medical Economics Co., Inc., Oradell, N.J.
Mao et al, "Monoclonal Antibodies to human ... I", Clinical Chemistry, vol. 29, No. 11, 1983, pp. 1890–1897.
Mao et al, "Monoclonal Antibodies to human . . . II", Clinical Chemistry, vol. 29, No. 11, 1983 pp. 1898–1903.
Miller, "High Density Lipoproteins and Atherosclerosis", Ann. Rev. Med. 1980 31:97–108.
Mao et al, "Immunochemistry of human plasma high density lipoproteins ... " Biochemistry, 1975, 14, pp. 4127.
Badimon et al, "Quantification and immunolocalization of apolipoprotein E . . . ", Atherosclerosis, 61 (1986) 57–66.
Mao et al, "Immunochemistry of human plasma high density lipoproteins ... ", Biochemistry, vol. 14, No. 18, 1975, pp. 4127–4131.
Kita, et al., Proc. Natl. Acad. Sci. USA 84, 5928–31 (1987).

*Primary Examiner*—Paul J. Killos
*Attorney, Agent, or Firm*—Michael W. Ferrell

[57] ABSTRACT

This invention relates to the compounds of 2,6-di-t-butyl-4-[(dimethyl-4-methoxyphenylsilyl)methyloxy]phenol and 2,6-di-t-butyl-4-[(dimethyl-2-methoxyphenylsilyl) methyloxy]phenol, polymorphs thereof and their pharmaceutically acceptable salts, useful as antiatherosclerotic agents.

9 Claims, No Drawings

2,6-DI-T-BUTYL-4-[(DIMETHYL-4-METHOXYPHENYLSILYL)-METHYL-OXY]PHENOL AND 2,6-DI-T-BUTYL-4-[(DIMETHYL-2-METHOXY-PHENYLSILYL)METHYLOXY]PHENOL

This Application claims the benefit of U.S. Provisional Application Ser. No. 60/080,226, filed Jun. 25, 1997.

BACKGROUND OF THE INVENTION

U.S. Pat. No. 5,155,250, issued Oct. 13, 1992 and U.S. Pat. No. 5,532,400, issued Jul. 2, 1996 disclose a class of compounds which are described by the following formula:

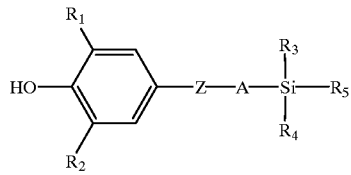

wherein $R_1$, $R_2$, $R_3$ and $R_4$ are each independently a $C_1$–$C_6$ alkyl group; Z is a thio, oxy or methylene group; A is a $C_1$–$C_4$ alkylene group; $R_5$ is a $C_1$–$C_6$ alkyl or —$(CH_2)_n$—(Ar) wherein n is an integer 0, 1, 2 or 3; and Ar is phenyl or naphthyl unsubstituted or substituted with one to three substituents selected from the group consisting of hydroxy, methoxy, ethoxy, chloro, fluoro or $C_1$–$C_6$ alkyl. These patents state that the compounds are antioxidants which inhibit low density lipoprotein (LDL) lipid peroxidation and are useful as antiatherosclerotic agents. Preferred compounds of these patents include those in which $R_1$ and $R_2$ are tertiarybutyl; $R_3$ and $R_4$ are methyl or ethyl; Z is thio; A is methylene; and wherein $R_5$ is methyl, ethyl or substituted or unsubstituted phenethyl. A particularly preferred disclosed compound of the above formula is 2,6-di-t-butyl-4-[(dimethylphenylsilyl)methyl]thiophenol.

SUMMARY OF THE INVENTION

The present invention is directed to the compounds 2,6-di-t-butyl-4-[(dimethyl-4-methoxyphenylsilyl)methyloxy]phenol and 2,6-di-t-butyl-4-[(dimethyl-2-methoxyphenylsilyl)methyloxy]phenol, a polymorph or a pharmaceutically acceptable salt thereof. Other aspects of this invention are directed to pharmaceutical compositions containing these compounds and the antiathero-sclerotic use of these compounds. 2,6-Di-t-butyl-4-[(dimethyl-4-methoxyphenylsilyl)methyloxy]phenol (Compound I) and 2,6-di-t-butyl-4-[(dimethyl-2-methoxyphenylsilyl)methyloxy]phenol (Compound II) can be represented by the following formulae:

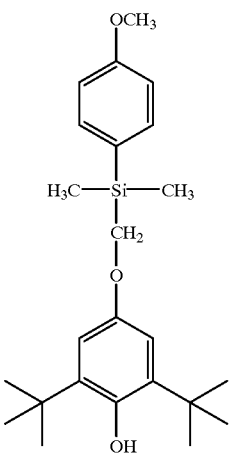

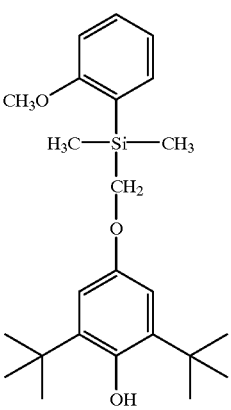

These compounds and their methods of preparation are generically described in U.S. Pat. No. 5,155,250, issued Oct. 13, 1992 and U.S. Pat. No. 5,532,400, issued Jul. 2, 1996. These patents do not specifically name 2,6-di-t-butyl-4-[(dimethyl-4-methoxyphenylsilyl)methyloxy]phenol nor 2,6-di-t-butyl-4-[(dimethyl-2-methoxyphenylsilyl)methyloxy]phenol, nor do they specifically exemplify the preparation of these compounds.

DETAILED DESCRIPTION OF THE INVENTION

As used herein, the term "pharmaceutically acceptable salt" refers to a basic addition salt. The expression "pharmaceutically acceptable basic addition salts" is intended to apply to any non-toxic organic or inorganic basic addition salts of the compounds represented by the formulae (I) or (II) or any of their intermediates. Illustrative bases which form suitable salts include alkali metals or alkaline-earth metals hydroxides such as, sodium, potassium, calcium, magnesium, or barium hydroxides; ammonia and aliphatic, cyclic, or aromatic organic amines such as methylamine, dimethylamine, trimethylamine, and picoline.

As used herein, the term "polymorph" refers to a solid crystalline phase of a compound represented by the formulae (I) or (II) or any of their intermediates, resulting from the possibility of at least two different arrangements of the molecules of the compound in the solid state. Polymorphs of a given compound will be different in crystal structure but identical in liquid or vapor states. Moreover, solubility, melting point, density, hardness, crystal shape, optical and electrical properties, vapor pressure, stability, etc., may all vary with the polymorphic form. Remington's Pharmaceutical Sciences, 18th Edition, Mack Publishing Co. (1990), Chapter 75, pages 1439–1443.

The compounds 2,6-di-t-butyl-4-[(dimethyl-4-methoxyphenylsilyl)methyloxy]-phenol and 2,6-di-t-butyl-4-[(dimethyl-2-methoxyphenylsilyl)methyloxy]phenol can be prepared by utilizing procedures and techniques known in the art as was discussed in U.S. Pat. Nos. 5,155,250 and 5,532,400. A general synthetic scheme for preparing the compounds of this invention are set forth in Scheme A.

SCHEME A

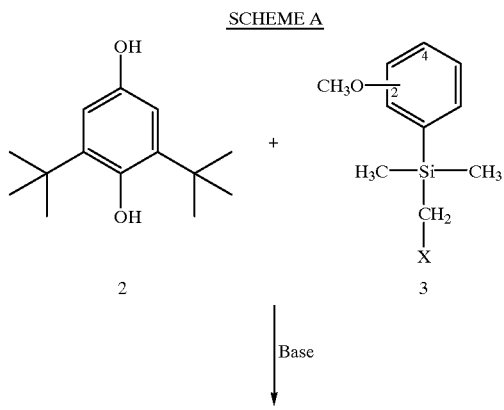

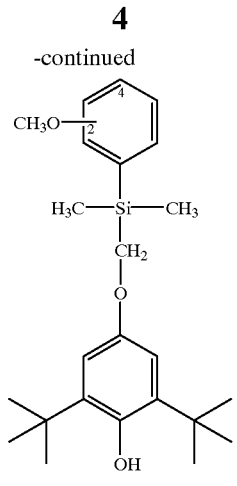

X = chlorine, bromine, or iodine (IA)

In Scheme A, the phenol of structure IA includes the compounds of formula I and II disclosed above, wherein the methoxy substituent is attached at either the 2- or 4-position. In general, a phenol of structure IA can be prepared by reacting 2,6-di-t-butylhydroquinone of structure 2 (or suitably protected derivatives) with a non-nucleophilic base, such as sodium hydride, potassium carbonate or cesium carbonate, and the appropriate haloalkylenesilane of structure 3, such as the appropriate chloroalkylenesilane, in a suitable aprotic solvent, such as acetonitrile, dimethylformamide or dimethylacetamide, or in an aqueous solvent, such as water/2-butanone.

The haloalkylenesilane starting materials of structure 3 may be prepared by utilizing procedures and techniques well known and appreciated by one of ordinary skill in the art. A general synthetic scheme for preparing the starting materials of structure 3, wherein the methoxy radical is in the 2-position is set forth in Scheme B.

SCHEME B

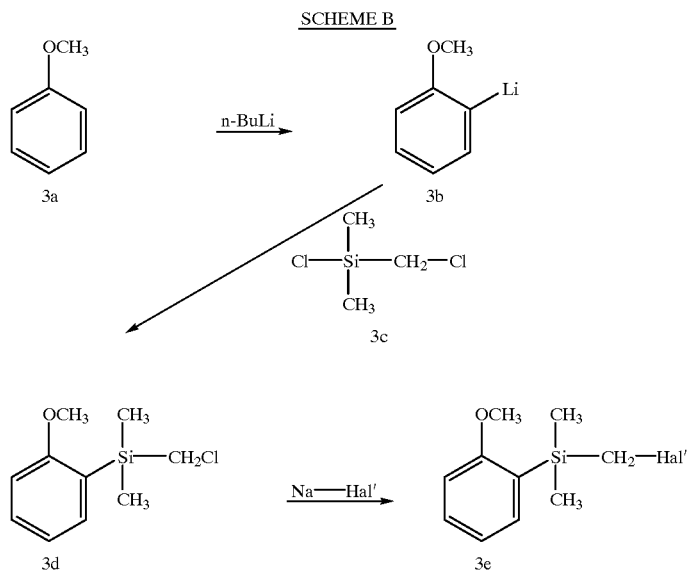

Hal' = bromine or iodine

In general, anisole 3a may be lithiated in a suitable organic solvent, such as diethyl ether, by reaction with n-butylithium. The lithio compound formed, structure 3b, is reacted with the chlorodimethylsilane of structure 3c to give the chloromethyldimethyl-2-methoxyphenyl silane of structure 3d. The chloromethyldimethyl-2-methoxyphenyl silane of structure 3d optionally may be reacted with Na–Hal' to form the compound of structure 3e. Prefereably sodium iodide or potassium iodide is reacted with the compound of structure 3d to form the iodo derivative of the structure of 3d.

A general synthetic scheme for preparing the starting materials of structure 3, wherein the methoxy radical is in the 4-position is set forth in Scheme C.

SCHEME C

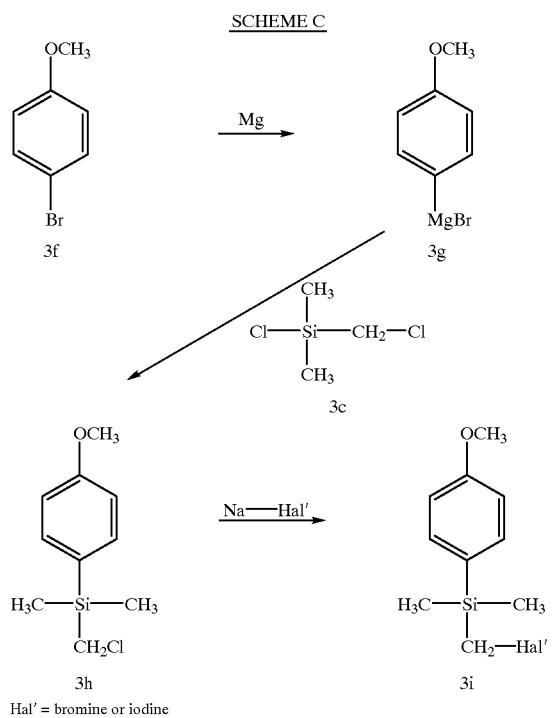

Hal' = bromine or iodine

In general, 4-bromoanisole of structure 3f is reacted with magnesium metal to form the Grignard reagent of structure 3g. The Grignard reagent of structure 3g is then reacted with the chlorodimethylsilane of structure 3c to give the chloromethyldimethyl-4-methoxyphenyl silane of structure 3h. The compound of structure 3h optionally may be reacted with Na—Hal' to form the compound of structure 3i. Preferably sodium iodide or potassium iodide is reacted with the compound of structure 3h to form the iodo derivative of the structure of 3i.

In those instances where the 1-phenol functionality of a compound of structure 2 may react with the compounds of structure 3 under the conditions of the reaction, the 1-phenol functionality of compound of structure 2 may be blocked with standard phenol blocking agents which are well known and appreciated in the art. The selection and utilization of particular blocking groups are well known to one of ordinary skill in the art. In general, blocking groups should be selected which adequately protect the phenol in question during subsequent synthetic steps and which are readily removable under conditions which will not cause degradation of the desired product.

Examples of suitable phenol protecting groups are ethers, such as methoxymethyl, 2-methoxyethoxymethyl, tetrahydro-pyranyl, t-butyl and benzyl; silyl ethers, such as trimethylsilyl and t-butyldimethylsilyl; esters, such as acetate and benzoate; carbonates, such as methylcarbonate and benzylcarbonate; as well as sulfonates, such as methanesulfonate and toluenesulfonate.

It is preferred that the reaction of Scheme A be conveniently carried out without blocking of the 1-phenol functionality.

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "° C." refers to degrees Celsius; "mm Hg" refers to millimeters of mercury; "mp" refers to melting point; "mg" refers to milligrams; "$\mu$M" refers to micromolar; "$\mu$g" refers to micrograms.

EXAMPLE 1

2,6-Di-t-butyl-4-[(dimethyl-4-methoxyphenylsilyl)-methyloxy]phenol

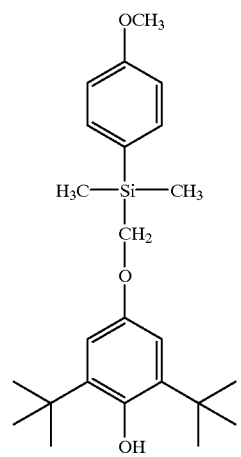

(a) Preparation of Dimethyl-p-methoxyphenylchloromethyl silane

Scheme C; Activate magnesium metal (12 g, 0.05 mol) by stirring with an overhead stirrer for 18 h in an inert atmosphere. Add a crystal of iodine and add a solution of dimethylchloromethylchlorosilane (8.1 g, 0.05 mol) in THF (100 mL) at a rate which maintains a reaction temperature below reflux. Pour the reaction mixture into aqueous ammonium chloride/ether. Separate the organic layer, dry and evaporate. Distill the residue using a Kugelrohr distillation apparatus to give the product, bp 90–96° C. in 52% yield. Anal: Calcd for $C_{10}H_{15}ClOSi$: C, 55.93; H, 7.04 Found: C, 55.40; H, 7.15

(b) Preparation of 2 6-Di-t-butyl-4-[(dimethyl-4-methoxyphenylsilyl)-methyloxy]phenol Scheme A; Reflux 2,6-di-t-butylbenzhydroquinone (13.7 g, 61.1 mmol), potassium carbonate (9.4 g, 68 mmol), dimethyl-p-methoxyphenylchloromethyl silane (14.6 g, 68 mmol) and a catalytic amount of potassium iodide in acetonitrile (200 mL) for three days under $N_2$. Filter off solids and evaporate. Redissolve in ethyl acetate and wash with water, then brine, dry with anhydrous magnesium sulfate, filter and evaporate. The resulting orange oil can be purified by distilling to 135° C. @ 0.1 mm Hg to remove lower boiling impurities followed by distillation of product (bp 155–165°

C. @ 0.1 mm Hg). The product which crystallizes on standing can be recrystallized from hexane to give a white solid (4.9 g, 19% yield) mp 122–123° C.

Anal. Calcd. for $C_{24}H_{36}O_3Si$: C, 71.95; H, 9.06

Found: C, 71.80; H, 9.00

NMR (CDCl$_3$): 7.53 (d, 2H, J 8.6), 6.93 (d, 2H, J8.6), 6.80 (s, 2H), 4.71 (s, 1H), 3.81 (s, 3H), 3.70 (s, 2H), 1.42 (s, 18H), 0.39 (s, 6H).

EXAMPLE 2

2,6-Di-t-butyl-4-[(dimethyl-2-methoxyphenylsilyl)-methyloxy]phenol

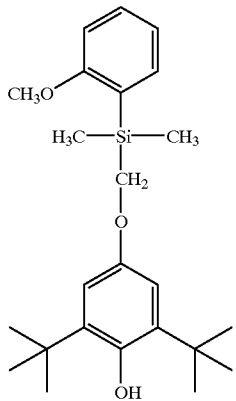

(a) Preparation of Dimethyl-o-methoxyphenylchloromethylsilane

Scheme B; Dissolve anisole (21.6 g, 0.2 mol) and N,N,N$^+$,N$^+$-tetramethylethylene-diamine (23.2 g, 0.2 mol) in ether (700 mL), chill the in an ice bath and add n-butyllithium (100 mL, 2.5 molar in hexane). Stir the mixture overnight at ambient temperature. Chill the mixture in an ice bath and add dropwise a solution of chloromethyldimethylchlorosilane (28.6 g, 0.2 mol) in ether (100 mL). Remove the ice bath and stir the mixture for another 4 h at ambient temperature. Pour the reaction mixture onto aqueous ammonium chloride (500 mL) and separate the organic layer, dry and evaporate. Distill the residue to give the product as a clear colorless liquid (27.2 g, 63%), bp 90–91° C. @ 1 mm.

Anal: Calcd for $C_{10}H_{15}ClOSi$: C, 55.93; H, 7.04

Found: C, 56.05; H, 7.02

(b) Preparation of 2,6-Di-t-butyl-4-[(dimethyl-2-methoxyphenylsilyl)-methyloxy]phenol Scheme A; Heat a mixture of dimethyl-o-methoxyphenylchloromethylsilane (27.2 g, 0.127 mol), sodium iodide (19 g, 0.127 mol) and acetonitrile (350 mL) at reflux for 28 h. Cool the mixture to ambient temperature and add 2,6-di-t-butyl-1,4-hydroquinone (31.5 g, 0.14 mol) and potassium carbonate (20.8 g, 0.15 mol). Reflux the mixture under a nitrogen atmosphere for 7 days. Cool the mixture and pour into water (400 mL) and ethyl acetate (400 mL). Separate the organic layer, evaporate the organic layer and chromatograph the residue on silica gel (hexane/ethyl acetate 9/1). Recrystallize (methanol) the chromatographed product to give the product (15.6 g, 31%) as a white solid, mp 89–90° C.

Anal. Calcd for $C_{24}H_{36}O_3Si$: C, 71.95; H, 9.06

Found: C, 71.84; H, 9.05.

EXAMPLE 3

Alternative Preparation of 2,6-Di-t-butyl-4-[(dimethyl-2-methoxyphenylsilyl)-methyloxy]phenol

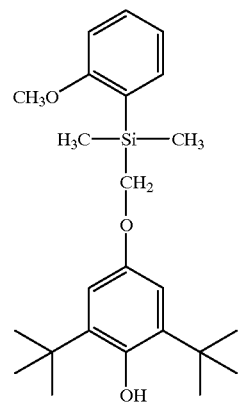

Dissolve dimethyl-o-methoxyphenylchloromethylsilane (800 g, 3.73 mol, Example 2, step a) in acetonitrile (4 L), add sodium iodide (555 g, 3.73 mol) and heat the mixture at reflux under a nitrogen atmosphere for 4 h. Cool the mixture to ambient temperature and add a solution of 2,6-di-t-butylhydroquinone (830 g, 3.73 mol) in acetonitrile (1 L). Bubble nitrogen through the resulting mixture for 30 min to eliminate oxygen. Add cesium carbonate (1212 g, 3.73 mol) and heat the mixture at reflux for 5 days. Cool the mixture to ambient temperature and add aqueous ammonium chloride (3 L) and ethyl acetate (2.5 L). Dry the organic layer and evaporate. Recrystallize the residue from an equal volume of methanol. Evaporate the filtrate and heat the residue on a Kugelrohr distillation apparatus at 90° C. (1 mm) for 2 hours to distill off byproducts. Recrystallize the residue from an equal volume of methanol. Combine all of the batches of recrystallized material and perform a second recrystallization from an equal volume of methanol. Repeat the recrystallization to give 437.5 g of product, mp 97–98° C.

Anal: Calcd for $C_{24}H_{36}O_3Si$: C, 71.95; H, 9.06

Found: C, 71.64; H, 8.96

As noted above, the compounds of this invention are antiatherosclerotic compounds. One method of demonstrating the antiatherosclerotic utility of these compounds is via the following in vivo rabbit model set forth in Example 4.

EXAMPLE 4

Antiatherosclerotic Effects of Compounds I and II Compared With a Prior Art Compound in Cholesterol-Fed Female New Zealand White Rabbits A. Experimental Protocol Female New Zealand White rabbits (Hazelton, ~2.0–2.3 kg) were fed 0.5% cholesterol/10% corn oil enriched rabbit chow (Purina # 5322) with or without test compound. The experiment was conducted for 70 days. The test compounds were solubilized in 100% ethanol and sprayed on the chow; control chows were sprayed with ethanol. The chows were dried overnight in a chemical fume hood. Rabbits were fed 100 grams food per day; water was available ad libitum. On the last day of the study rabbits (fasted overnight) were bled (~2 mL) from a marginal ear vein periodically to monitor serum cholesterol levels. The rabbits were euthanized on day 70 by carbon dioxide overdose. The total body and liver weights were recorded in grams. Food consumption was recorded as grams•day$^{-1}$. Aliquots of fresh serum were used for clinical chemistries and copper induced thiobarbituric acid reactive substances (TBARS). Aliquots of serum and livers (~5 gram) were frozen at −20° C. for compound and metabolite concentration determination at a later time.

B. Aorta Staining and Lesion Quantitation

The aortas were dissected from rabbits immediately after they were killed. The aorta from the ascending arch to the iliac bifurcation was excised after debridement of extraneous adipose tissue. Aortas were stored overnight in phosphate buffered saline (PBS)/0.02% sodium azide, pH 7.4, at 4° C. until final debridement. Before staining, aortas were cut open longitudinally and stained with Sudan IV as follows. Sudan IV stain (5.0 g) was added to 500 mL of 70% ethanol, 500 mL of acetone were added, and the solution was stirred overnight at room temperature. The solution was filtered through Whatman #1 filter paper. Aortas were rinsed with 70% ethanol for 10 minutes. They were stained with Sudan IV for 60 min at room temperature, rinsed with 70% ethanol for 5–10 min, and stored in deionized water overnight at 4° C. They were stored in PBS/0.02% sodium azide at 4° C. until imaging could be completed.

The areas containing sudanophilic lesions were quantitated as follows. Aortas were pinned flat onto black plastic sheets, illuminated with several fiber optic light sources, and photographed with a KODAK DCS-420 digital camera mounted on a copy stand. Images were captured and converted to 24 bit color TIFFs with Image Pals image editor software. The resulting images were rescaled to 1024×683 pixels to permit input into the Simple image analysis system and transferred to optical disk storage media. The Simple software was programmed to allow a region of interest to be drawn around the section of the aorta (arch, thoracic, abdominal) which separated the image of the aorta from the pins and the background. the program determined the tissue area in pixels based on pre-selected thresholds of hue, saturation, and intensity. These thresholds were adjusted to recognize the lesion area, and the percent fraction (# lesion pixels/# tissue pixels) was determined. This process was repeated on each portion of the aorta for each rabbit.

C. Clinical Chemistries

Blood was allowed to clot at room temperature for 30 minutes. Serum was obtained after centrifugation for 10 min at 5° C. at 3000 rpm in a Beckman GPKR centrifuge with a GH 3.7 rotor. Fresh serum was analyzed by a COBA MIRA S autoanalyzer (Roche Diagnostics) using Roche diagnostic reagents for total cholesterol (CHOL, kit # 44334) and triglyceride (TG, kit # 44120). Cholesterol and triglycerides were calculated as mg/dL.

D. TBARS Assay

TBARS are a qualitative indication of the oxidation of lipids in a sample. Mao, S J T et al. *Meth. of Enzymol.* 234, 517–525 (1994). In this assay copper sulfate was used to initiate the oxidation serum lipids, resulting in the formation of aldehydes, such as malondialdehyde (MDA). Upon incubation with thiobarbituric acid, the absorbance of the aldehydes was detected at 530–540 nm. TBARS values which are lower than control serum values indicate the relative ability of a test compound to inhibit the oxidation. TBARS were measured as follows: 50 µL of serum were mixed with 50 µL of 0.9% saline and 400 µL of a 5 mmol $CuSO_4$ solution and incubated at 37° C. for 5 hr. The reactions were stopped by addition of 1.0 mL of 20% trichloroacetic acid. Then 1.0 mL of 0.67% thiobarbituric acid in 0.05 N sodium hydroxide was added, mixed, and the samples incubated for 30 min at 90° C. Samples were centrifuged briefly to pellet undissolved material and the supernatants were transferred to a 96-well microtiter plate. Absorbances were measured at 540 nm using a Biotek model EL311 microplate reader. The nmoles of MDA produced were calculated from a standard curve of 0 to 10 nmoles of MDA prepared from malonaldehyde bis(dimethyacetal). Serum samples from treated rabbits were compared to serum samples from control rabbits that received no test compound.

E. HPLC—Quantitation of Serum and Liver Compound and Metabolite Concentration

Serum and liver concentrations of parent compounds and the metabolites, bisphenol and diphenoquinone, were determined by reverse phase HPLC using a Waters 990 Powerline system. Mao, S. J. T. et al., *Meth. of Enzymol.* 234, 517–525 (1994); Satoni, D. K. and Coutant, J. E., *J. Chrom.* 380, 401–406 (1986). Livers (1 gram) were homogenized with 5.0 mL PBS, pH 7.4, using a Polytron tissue homogenizer at setting 5 for 20–30 seconds. Serum or liver homogenates were extracted as follows: 100 µL of serum or homogenate were added to 2.0 mL diethyl ether: ethanol (3:1) while vortexing the tube. The sample tubes were capped and centrifuged for 10 min at 5° C. at 3500 rpm in a Beckman GPKR centrifuge with a GH 3.7 rotor. The supernatants were transferred to clean tubes and dried under $N_2$. Samples were reconstituted with 200 µL of acetonitrile:hexane:0.1 M ammonium acetate (90:6.5:3.5, by vol.). Then, 100 µL were injected onto a Waters Deltapak C18–300 Å column, and eluted with an 83% acetonitrile: 17% water mobile phase at a flow rate of 1.5 mL/min. Absorbances at the wavelengths of 240, 254, and 420 nm were recorded. Compound concentrations were calculated from known quantities of authentic parent compounds after correction for recovery; the range of recovery from spiked samples was 40 to 100%. The lowest detectable limit for this class of compounds was ~0.5 µg/mL. Concentrations were calculated as of µg/mL serum and of µg/mL liver.

2,6-Di-t-butyl-4-[(dimethyl-4-methoxyphenylsilyl) methyloxy]phenol and 2,6-di-t-butyl-4-[(dimethyl-2-methoxyphenylsilyl)methyloxy]phenol were tested in this in vivo procedure. For comparative purposes, 2,6-di-t-butyl-4-[(dimethylphenylsilyl)methylthio]phenol was also tested. This compound was prepared and described in U.S. Pat. No. 5,155,250 and U.S. Pat. No. 5,532,400. Tables 1 and 2 illustrate the obtained results. For the purposes of Tables 1 and 2, Compound I corresponds to 2,6-Di-t-butyl-4-[(dimethyl-4-methoxyphenylsilyl)methyloxy]phenol, Compound II corresponds to 2,6-di-t-butyl-4-[(dimethyl-2-methoxyphenylsilyl)methyloxy]phenol and Compound III corresponds to 2,6-di-t-butyl-4-[(dimethylphenylsilyl) methylthio]phenol.

TABLE 1

Antiatherosclerotic Effects of Compounds 1 and 2 of the Invention Versus Compound 3 of the Prior Art in Cholesterol-Fed Female New Zealand White Rabbits as a Percent of Control

| Cmpd. No. | No. of Rabts. | Diet % Cmpd. | body wt. | lw/bw | chol tot. | TRIG | TBARS | Aortic Lesion % of Area | | | |
|---|---|---|---|---|---|---|---|---|---|---|---|
| | | | | | | | | Total | Arch | Thor. | Abdom. |
| I | 13 | 0.15* | 95% | 89% | 28% | 22% | 56% | 4% | 5% | 3% | 10% |
| II | 13 | 0.40 | 98% | 86% | 79% | 100% | 90% | 55% | 56% | 44% | 50% |
| III | 6 | 0.40 | 89% | 98% | 64% | 783% | 18% | 43% | 50% | 30% | 30% |

*Compound I was given at 0.4% × 7 days, 0% × 7 days, then 0.15% × 56 days
Diet % = (weight sample compound/weight food) × (100)
The data in TABLE 1 were normalized as follows:
% Control = (Mean, treated group / Mean, control group) × (100)
Body wt. = weight in kilograms
liver wt. = weight in kilograms
LW/BW = (liver weight / body weight)
CHOL = total cholesterol mg/dL
TRIG = triglycerides, mg/dL
TBARS = thiobarbituric acid reactive substances, expressed as nmole MDA
Aortic Lesions:
Total = % area of total surface area of aorta covered with lesions
Arch, Thoracic, Abdominal = % area of each segments of the aorta As indicated in Table 1, Compounds I–III all decreased serum cholesterol, TBARS and the amount of aortic lesions in comparison with control rabbits. However, while Compound III reduced total aortic lesions by 57%, Compound I reduced total aortic lesions an average of 96% when administered at a lower dose than Compound III (0.15% for Compound I compared to 0.4% for Compound III). Moreover, Compounds I and II did not show an undesirable increase of triglycerides, whereas the triglyceride count for Compound III climbed to 783%.

TABLE 2

Drug and Metabolite Concentration in Rabbit Serum and Liver

| Compound No. | Diet % | Parent | Serum Bis | Quin | Parent | Liver Bis | Quin |
|---|---|---|---|---|---|---|---|
| I | 0.15* | 7.3 | 0 | 0 | 44.9 | 0 | 0 |
| II | 0.40 | 93.3 | 0 | 0 | 80.9 | 0 | 0 |
| III | 0.40 | 182.4 | 43.4 | 134.1 | 323.0 | 163.6 | 64.4 |

*Compound I was given at 0.4% × 7 days, 0% × 7 days, then 0.15% × 56 days
Diet % = (weight sample compound/weight food) × (100)
Sample compound concentrations in serum and liver are presented as $\mu g/mL$ or $\mu g/g$, respectively.
Serum Parent = parent compound concentration as $\mu g/mL$ of serum
Serum Bis = bisphenol concentration as $\mu g/mL$ of serum
Serum Quin = diphenoquinone concentration as $\mu g/g$ serum
Liver Parent = parent compound concentration as $\mu g/g$ liver
Liver Bis = bisphenol concentration as $\mu g/g$ liver
Liver Quin = diphenoquinone concentration as $\mu g/g$ liver
0 = value less than detectable limit of HPLC system As indicated in Table 2, Compound III was found in very high concentrations in the serum (182.4 $\mu g/mL$) and livers (323.0 $\mu g/mL$). In contrast, Compound I was found in minute concentrations in the serum (7.3 $\mu g/mL$) with a small amount in the livers (44.9 $\mu g/mL$) while Compound II was found in moderate amounts in serum and livers (93.3 $\mu g/mL$, 80.9 $\mu g/mL$) but much lower than Compound III.

Moreover, the bisphenol and diphenoquinone metabolites of Compound III were also found in undesirably high concentrations in both serum and livers. In contrast, none of the bisphenol and diphenoquinone metabolites of Compounds I or II were detected in either serum or livers.

As used herein, the term "patient" refers to a warm-blooded animal or mammal which is in need of treatment for atherosclerosis. It is understood that guinea pigs, dogs, cats, rats, mice, hamsters, rabbits and primates, including humans, are examples of patients within the scope of the meaning of the term.

Atherosclerosis is a disease state characterized by the development and growth of atherosclerotic lesions or plaque. The identification of those patients who are in need of treatment for atherosclerosis is well within the ability and knowledge of one of ordinary skill in the art. For example, individuals who are either suffering from clinically significant atherosclerosis or who are at risk of developing clinically significant atherosclerosis are patients in need of treatment for atherosclerosis. A clinician of ordinary skill in the art can readily determine, by the use of clinical tests, physical examination and medical/family history, if an individual is a patient in need of treatment for atherosclerosis.

An effective antiatherosclerotic amount of a compound of formulae (I) or (II) is an amount which is effective, upon single or multiple dose administration, in inhibiting the development or growth of atherosclerosis in a patient in need thereof. As such, successful treatment of a patient for atherosclerosis is understood to include effectively slowing, interrupting, arresting, or stopping atherosclerotic lesion or plaque development or growth and does not necessarily indicate a total elimination of atherosclerosis. It is further understood and appreciated by those of ordinary skill in the art that successful treatment for atherosclerosis can include prophylaxis in preventing atherosclerotic lesion or plaque formation.

In determining the effective antiatherosclerotic amount of a compound of formulae (I) or (II), a number of factors are considered by the attending diagnostician, including, but not limited to: the species of the mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

An effective antiatherosclerotic amount of a compound of formulae (I) or (II) will generally vary from about 1 milligram per kilogram of body weight per day (mg/kg/day) to about 5 grams per kilogram of body weight per day (gm/kg/day). A daily dose of from about 1 mg/kg to about 500 mg/kg is preferred.

In effecting treatment of a patient, a compound of formulae (I) or (II) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the disease state to be treated, the stage of the disease, and other relevant circumstances. Remington's Pharmaceutical Sciences, 18th Edition, Mack Publishing Co. (1990).

A compound of formulae (I) or (II) can be administered in the form of pharmaceutical compositions or medicaments which are made by combining a compound of formulae (I) or (II) with pharmaceutically acceptable carriers or excipients, the proportion and nature of which are determined by the chosen route of administration, and standard pharmaceutical practice.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, a compound of formulae (I) or (II) may be incorporated with excipients and used in the form of tablets, troches, capsules, elixirs, suspensions, syrups, wafers, chewing gums and the like. These preparations should contain at least 4% of a compound of formula (I) or (II), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, a compound of formulae (I) or (II) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants depending on the solubility and other properties of a compound of formula (I) or (II): sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

What is claimed is:

1. A compound selected from the group consisting of 2,6-di-t-butyl-4-[(dimethyl-4-methoxyphenylsilyl)methyloxy]phenol and 2,6-di-t-butyl-4-[(dimethyl-2-methoxyphenylsilyl)methyloxy]phenol, a polymorph or a pharmaceutically acceptable salt thereof.

2. A compound according to claim 1 wherein said compound is of 2,6-di-t-butyl-4-[(dimethyl-4-methoxyphenylsilyl)methyloxy]phenol.

3. A compound according to claim 1 wherein said compound is 2,6-di-t-butyl-4-[(dimethyl-2-methoxyphenylsilyl)methyloxy]phenol.

4. A pharmaceutical composition comprising a compound of claim 1 and a pharmaceutically acceptable carrier.

5. A pharmaceutical composition according to claim 4 wherein said compound is 2,6-di-t-butyl-4-[(dimethyl-4-methoxyphenylsilyl)methyloxy]phenol.

6. A pharmaceutical composition according to claim 4 wherein said compound is 2,6-di-t-butyl-4-[(dimethyl-2-methoxyphenylsilyl)methyloxy]phenol.

7. A method of inhibiting the progression of atherosclerosis in a patient in need thereof comprising administering to said patient an effective antiatherosclerotic amount of a compound of claim 1.

8. A method according to claim 7 wherein said compound is 2,6-di-t-butyl-4-[(dimethyl-4-methoxyphenylsilyl)methyloxy]phenol.

9. A method according to claim 7 wherein said compound is 2,6-di-t-butyl-4-[(dimethyl-2-methoxyphenylsilyl)methyloxy]phenol.

* * * * *